United States Patent [19]

Fukui et al.

[11] Patent Number: 5,303,025
[45] Date of Patent: Apr. 12, 1994

[54] EMISSION SPECTROCHEMICAL QUANTITATIVE ANALYSIS METHOD AND APPARATUS

[75] Inventors: Isao Fukui; Takao Miyama; Naoki Imamura, all of Kyoto, Japan

[73] Assignee: Shimadzu Corporation, Kyoto, Japan

[21] Appl. No.: 854,842

[22] Filed: Mar. 20, 1992

[30] Foreign Application Priority Data

Mar. 22, 1991 [JP] Japan ................. 3-83524

[51] Int. Cl.⁵ .................. G01N 21/63; G01N 21/67
[52] U.S. Cl. ..................... 356/313; 356/318
[58] Field of Search ............ 356/313, 317, 318

[56] References Cited

U.S. PATENT DOCUMENTS 4,326,801  4/1982  Ono et al. ............... 356/313

FOREIGN PATENT DOCUMENTS 0009766  4/1980  European Pat. Off. .
0203019  11/1986  European Pat. Off. .
3-48751  3/1991  Japan ................. 356/313
3138548  6/1991  Japan .

OTHER PUBLICATIONS

Abstract of Japanese Pat. Appln. 59-61 759, vol. 8, No. 165, 31 Jul. 1984 (Shimazu Seisakusho).
Concise explanation of Japanese Laid-Open Publication No. 3-138548.

Primary Examiner—F. L. Evans
Attorney, Agent, or Firm—Birch, Stewart, Kolasch & Birch

[57] ABSTRACT

A quantitative analysis of the constituents in a specimen and being classified by the conditions of the constituents in the specimen, using a spectroscopic analysis is made by exciting the specimen a number of times for emission, detecting the light intensity data of the line of the constituent element and the non-constituent element of the specimen per emission, storing the light intensity data of the lines specifying emission which contains the constituent element and the non-constituent element over a predetermined level based on the stored data, and determining that there is present a composition of the constituent element and the non-constituent element at a portion of the specimen corresponding to the specified emission.

11 Claims, 3 Drawing Sheets

EMISSION SPECTROCHEMICAL QUANTITATIVE ANALYSIS METHOD AND APPARATUS

BACKGROUND OF THE INVENTION

The present invention relates to a spectroscopic analyzing method and system in which the constituents of the sample are quantitatively analyzed with being classified by the conditions in the sample.

In the controlling the quality of the metal during smelting, it is necessary to analyze the constituents of the metal with classifying the conditions in the sample. The conditions of the constituents in the sample can be classified into two. One is the composite conditions such as nitrogen, oxide, and sulfide etc.

The other is the conditions of an alloy in which the elements are dispersed in a metal.

To analyze the constituents elements depending on the classification of the composite conditions and the alloy conditions, there are conventional chemical methods for separately analyzing using various solutions methods.

However, they are not rapid enough so that they cannot be effectively applied to controlling the method during smelting.

Thus quality control during smelting the metal is then difficult.

SUMMARY OF THE INVENTION

Accordingly, it is an object of the present invention to provide a relatively fast quantitative analysis of the constituents in a sample and being classified by the condition of the ingredients in the sample, using a spectroscopic analysis, so that quality control during smelting the metal is easily achieved.

Briefly described, in accordance with the present invention, a quantitative analysis of the constituents in a sample and being classified by the conditions of the sample is performed by a spectroscope analysis. For this purpose, the sample is excited a great number of times so as to emit. Each time the sample emits, the light intensity of the image regarding the ingredient elements and the non-constituent elements is detected to store the detected light intensity data of the lines. The light emission containing the constituent elements and the non-constituent elements over a predetermined level is specified.

Then, it is determined that there is present a composition of the constituent element and the non-constituent element in a region of the sample-corresponding to the specified emission. According to the present invention, speedy quantitative analysis of the constituents in the sample is achieved by a spectroscopic analysis. For example, the diameter of the spark discharge region of a single pulse by the spark discharge spectroscopic analysis is about $3\mu$.

The element in a metal consisting of a non-metal composition such as an oxide is generally present as an alloy component partially and another part of the element is formed as an oxide or a nitride. These non-metal compositions are deposited as interference material in the crystal boundary of the metal. Although the size of the interference material may be different from one another depending on its kind, the metal of Al or Ca in steel is melted into Fe and the oxide is $Al_2O_3$ and CaO, which are dispersed as the interference material with the size of about $5\mu$.

Therefore, the intensity of the spectra of Al and Ca produced by each single spark discharge substantially changes depending whether or not the discharge diameter encompasses an oxide, and what the size of the oxide is. This is because the melting elements of Al are dispersed in the metal in a small degree and if there is no interference material in the spark discharge region, the ratio of Al in the spark discharge region is small so that the light intensity of the line of Al is low and the charge of the light intensity of the liner per spark discharge is also small. However, if there is interference material in the spark discharge region, Al is gathered to the interference material and the ratio of Al in the spark discharge region is large so as to provide strong light intensity of the line of Al. The change of the light intensity is proportional to the amount of the interference material. The change of the given spectra intensity is several times to several hundred times. If there is an oxide of Al, the line due to oxygen of course appears.

Therefore, if the line due to oxygen is detected in a spark discharge it is assumed that the spark is generated from a region containing an oxide of the ingredients of the sample, and it is determined whether the light intensity of line of the ingredient elements of Al or Ca or the like shows an intensity more than the average intensity of each of the elements as a result of a great number of discharges. For example, if the light intensity of the line of Al is average and the light intensity of the line of Ca shows a predetermined value more than an average intensity, it can be determined that an oxide of Ca, CaO is contained in the spark region. On the contrary, if the light intensity of the line of Al shows a predetermined value more than the average intensity and the light intensity of the line of Ca is average, it can be determined that $Al_2O_3$ is contained in the spark region. If the light intensity of the line of Al and Ca is more than the average, it can be determined that both $Al_2O_3$ and CaO are contained in the spark region.

This can be applied to oxides and nitrides of Mg, Si, Ti, B and Zr, and metal compositions such as TiC etc.

The above described analysis can be made using spark discharges by excitement due to a laser beam. The laser beam can provide high analysis accuracy and a two-dimension map showing the conditions of the ingredients in the sample.

BRIEF DESCRIPTION OF THE DRAWINGS

The present invention will become more fully understood from the detailed description given hereinbelow and the accompanying drawings which are given by way of illustration only, and thus are not limitative of the present invention and wherein.

DESCRIPTION OF THE PREFERRED EMBODIMENT

Figure 1:
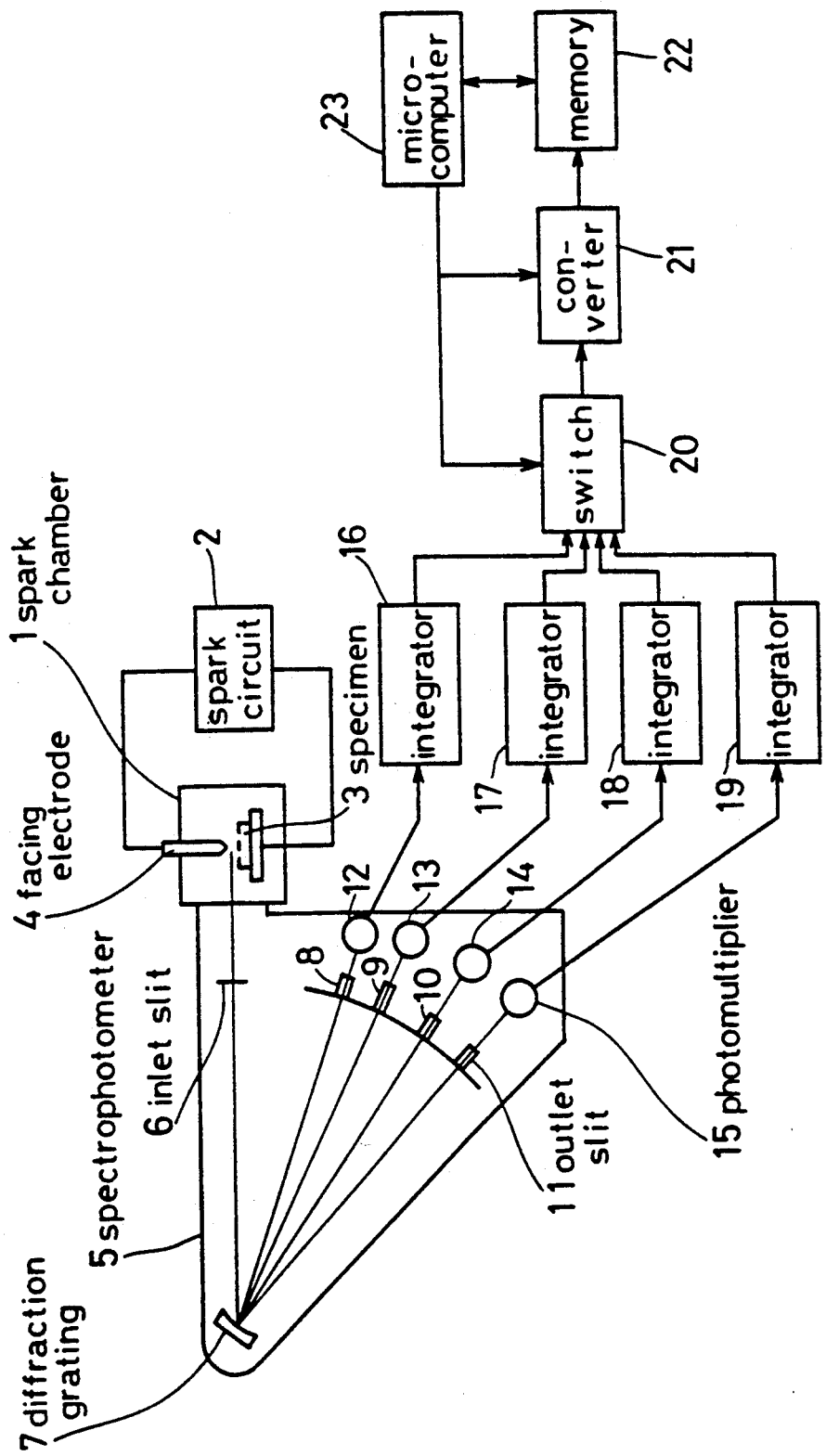
FIG. 1 is a block diagram of a spectroscopic analyzing system of the present invention in accordance with a preferred embodiment.
Figure 2A:
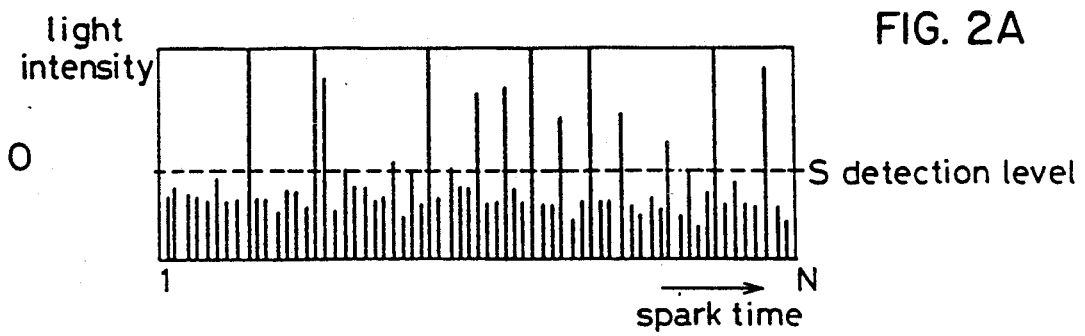
FIGS. 2(A)–2(D) are data given by the spectroscopic analyzing system of FIG. 1.
Figure 2B:
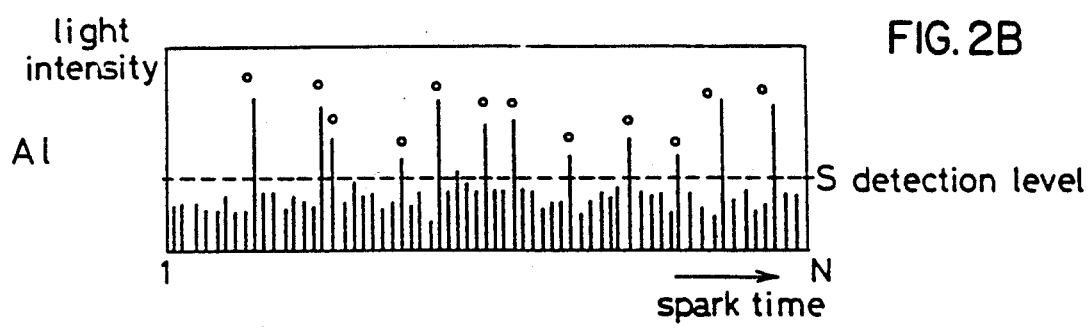
Figure 2C:
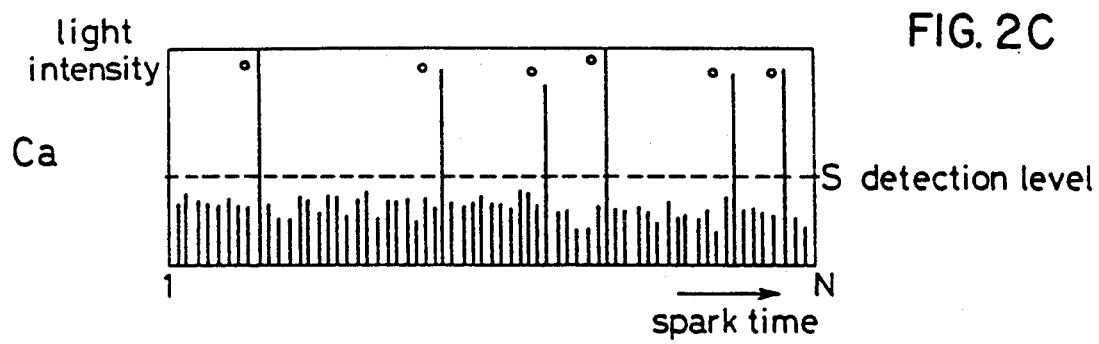
Figure 2D:
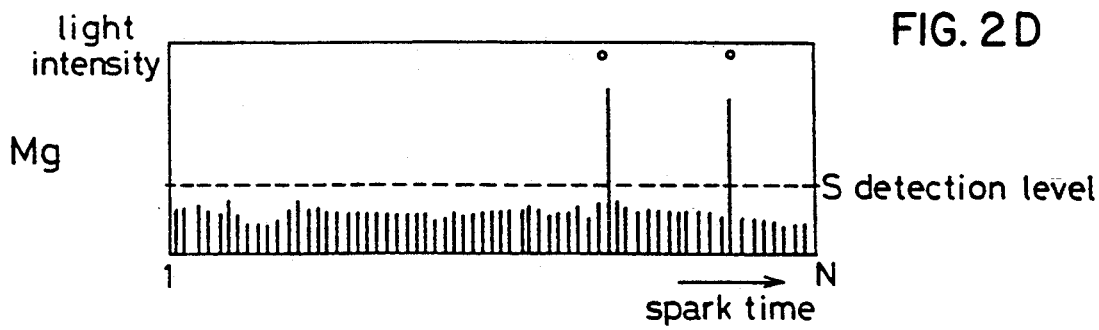

FIG. 1 shows a block diagram of an analyzing system according to the present invention. A spark chamber 1 is provided for sparking a specimen 3. The spark chamber 1 is filled with argon gas which is an inert gas. A spark discharge circuit 2 is operated to generate high voltage pulses for sparking a series of spark discharges. A high voltage pulse is applied between a facing electrode and the specimen 3 from the spark circuit 2 so that a spark discharge is generated between the facing electrode 4 and the specimen 3. A spectrophotometer 5 is provided whose contents are in a vacuum. An inlet slit 6 is used to receive parallel radiation from the spark light generated between the facing electrode 4 and the specimen 3. The parallel radiation is directed in a predetermined direction. A diffraction grating 7 is provided for providing spectroscopic analysis of the spark light from the inlet slit 6. Outlet slits 8 through 11 are positioned on the spectra image picture and the line position of each of the elements. Then, the spark discharge passing through each of the outlet slits 8 through 11 is only incident on photomultipliers 12 through 15. Individual pulse integrators 16 through 19 are provided for integrating light intensity signal of the line detected by the photomultipliers 12 through 15 at the unit of each spark discharge. Thus, a detection means is provided comprising the photomultipliers 12 through 15 and the single pulse integrators 16 through 19. A switch 20 is provided for subsequently forwardly the integration value of the (simple data, i.e. the data resulting from each spark discharge), integrated by the integrators 16 through 19 to an analog/digital (A/D) converter 21. The A/D converter 21 is operates to comment the received simple data to digital signals. A memory 22 is provided for storing the simple data subsequently in a predetermined area per element and storing the other data in another area. A microcomputer 23 is operated to control the respective elements and calculate the various data, which serves as the specifying means, the detection means and the prepare means of the present invention.

In operation, when the spark discharge circuit generates the voltage pulses at the facing electrode 4, the spark discharges between the specimen 3 and the facing electrode 4 are repeated one thousand to several thousand times to measure the light intensity for each of the elements at each spark discharge as shown in FIG. 2 (A) to 2 (D). In these figures, the length of the vertical bar at a position, at which the spark discharge order of each of the elements is the same, corresponds to the output signal of each of the single pulse integrators 16 through 19. The length of the vertical bar in each of the graphs at the same position indicates the light intensity of the line at one spark. The given light intensity data of the line of each of the elements are subsequently stored into the memory 22. From the data stored in the memory 22, the light intensity of the line per spark of the elements (O, Al, Ca, Mg etc.) is calculated into a percentage of the contents. The percentage of the contents is preliminarily determined in a detection line prepared by a reference sample with little interference material. Calculating the percentage of the contents enables analysis of the data by deleting a background. Thus, the average and dispersion value of the percentage of the contents of each of the elements per spark are determined, so that a composition detection level is set from the dispersion condition of the data. For example, the detection level is such that, assuming that the average content is $+3\sigma$, some element provides data more than this for a spark, it is determined that the spark region of that spark contains a composition or an interference material of that element.

FIG. 2 (A) shows the light intensity of the line of oxygen. For a spark discharge exceeding the detection level S, it is assumed that an oxide may be present and in the same spark discharge, the data of the other elements of Al, Ca, Mg etc. are checked to look for any other element exceeding the detection level. If there is a spark discharge over the detection level, it can be assumed that an oxide of that element is contained in that discharge. The spark discharges marked with a circle in FIGS. 2 (B) to 2 (D) are determined to contain an oxide of the element ($Al_2O_3$ for Al, CaO for Ca, and MgO for Mg). As shown in FIG. 2 (A), the reason why the emission of the line of oxygen is detected at each spark discharge is that the oxygen resolved into the metal is added to a simple backlight. Such a low level light intensity does not indicate the presence of an oxide. Of course, in principal, if the light intensity of the line of a metal element is over the predetermined level and there is the line of the oxygen, the oxide of that metal element can be considered to be present.

In a spark discharge whose region is assumed to contain an oxide, it will now be explained how to calculate the percentage of the content, Z% of the oxide of an oxidized element (for example, Al) in the spark region. At first, the content amount of the oxidized element in the spark discharge is determined from a detection line, so that the content amount in the spark region of that spark is A%. The average content of that element over the sample is B%. The gravity of an oxide of that element/the gravity of that element=C. Then, $$Z = (A - B) \times C.$$

The contents of the oxide in each of the elements at each of the sparks discharges an oxide of an element is specified to be contained are accumulated. The accumulated value is divided by all the spark discharge times of the single analysis to obtain the average value of the oxide of each of the elements. Using that average value, the content of the oxide of each f the elements in the whole of the sample is calculated. The average of the contents of each of the elements in sparks discharges other than the specified discharges is then determined. The average is outputted as the content of the simple substance of each element.

Figure 3:
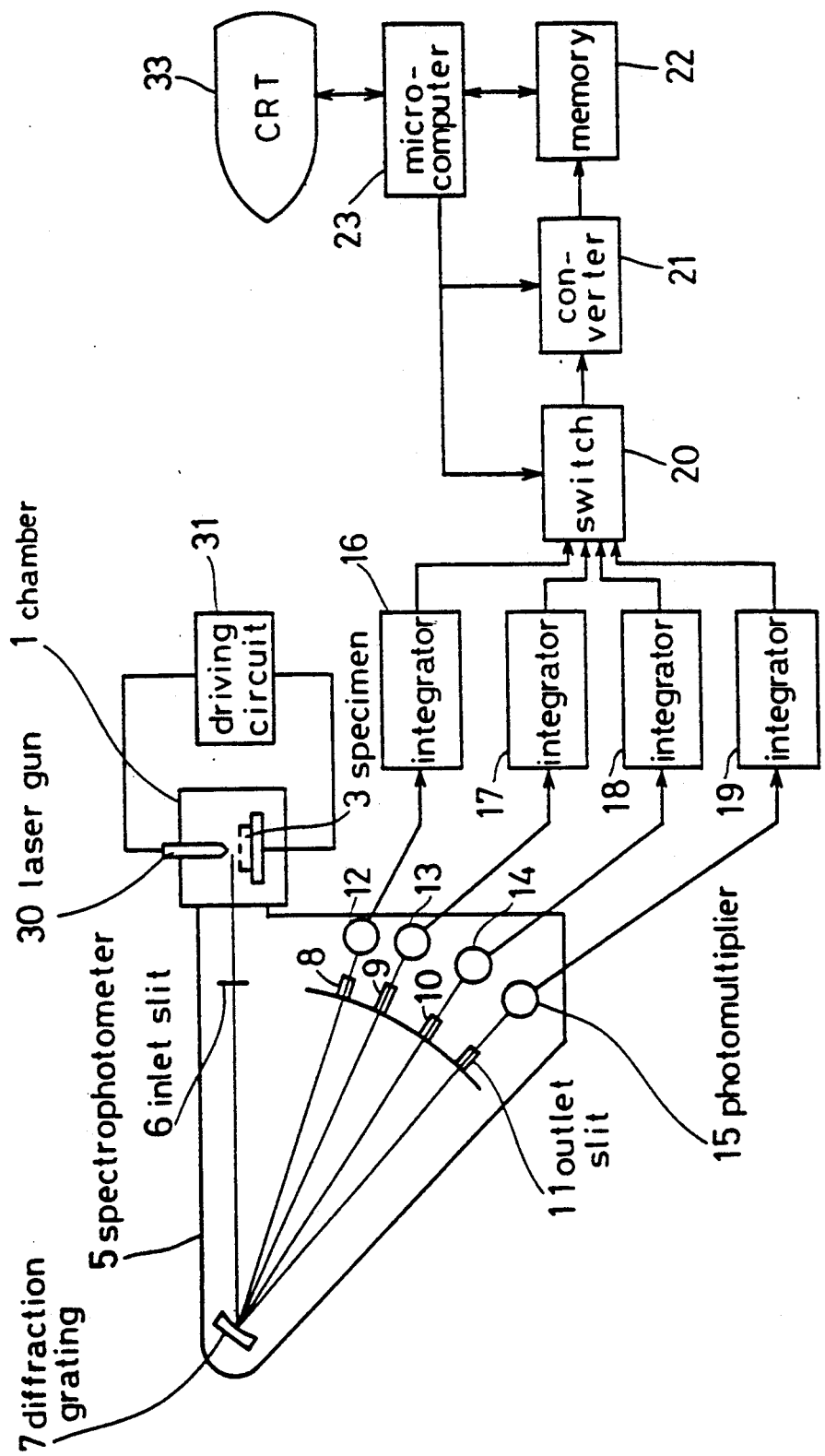
FIG. 3 is a block diagram of a spectroscopic analyzing system according to another preferred embodiment of the present invention.

FIG. 3 shows a block diagram of the spectroscopic analyzing system in another preferred embodiment of the present invention in which the facing electrode 4 is replaced by a laser gun 30 and the spark discharge circuit 2 is replaced by a laser gun driving circuit 31, a CRT 33 is connected as a display means to the microcomputer 23. The specimen 3 is excited by the laser beam. A two-dimensional map indicating the conditions in the specimen is displayed in the CRT 33. The other parts and the data processing operation are similar as the above embodiment. A suitable laser in this case is a $N_2$ laser beam which is featured by having short laser pulse and providing high output. When the $N_2$ laser beam is incident on a metal simple under the pressure lower than several torr, the white primary plasma having the small diameter and the secondary plasma which surrounds the white primary plasma in a semispheric form are both generated. The emission of the secondary plasma is used because the emission of the secondary plasma can provide high analysis accuracy without the influence of the background. The emission of the laser beam is expanded over the entire surface of the specimen with scanning. In the above embodiment using the spark discharge the discharge position of the spark discharge is randomed so that if the discharge position is shifted to a single point, it is impossible to obtain the uniform analysis results over the entire surface of the specimen 3. However, in this preferred embodiment, the emission of the laser beam is carried out with scanning the entire surface of the specimen 3. Here, the average analysis results over the entire surface of the specimen 3 can be assured in this embodiment. Further, the position information given by scanning the laser beam over the entire surface of the specimen 3 and the analysis results corresponding to the position information are composed to a two-dimensional map showing the conditions of the elements in the specimen 3. The two-dimensional map is prepared by the microcomputer 23 and displayed by the CRT 33. Then, the conditions of the elements in the specimen are visually presented.

As described above, according to the present invention, speedy quantitative analysis of the ingredients in the specimen with being classified by the conditions of the ingredients in the specimen is obtained using the spectroscopic analysis, so that quality control during smelting the metal is easily achieved.

While only certain embodiments of the present invention have been described, it will be apparent to those skilled in the art that various changes and modifications may be made therein without departing from the spirit and scope of the present invention as claimed.

What is claimed is:

1. A spectroscopic analyzing method comprising the steps of;

exciting a specimen a plurality of times and producing a spectral emissions thereby;

detecting the light intensity data of the spectral lines of the constituent element of said specimen and non-constituent element of said specimen for each emission;

storing the detected light intensity data of the lines;

specifying emission which contains said constituent element and said non-constituent elements over a predetermined level based on said stored data; and determining that a composite of the constituent element and the non-constituent element is present at a portion of said specimen corresponding to said specified emissions.

2. The spectroscopic analyzing method as set forth in claim 1, wherein said specifying step comprises a step of determining the contents of each of said elements based on the light intensity data of said lines and specifying the emission of a predetermined level of said contents.

3. The spectroscopic analyzing method as set forth in claim 2, wherein said predetermined level in said specifying step is selected in accordance with an average value and a dispersion value of the contents in each emission.

4. The spectroscopic analyzing method as set forth in claim 1, wherein said exciting step comprises a step of spark discharging said specimen.

5. The spectroscopic analyzing method as set forth in claim 1, wherein said exciting step comprises a step of using a laser for exciting said specimen.

6. A spectroscopic analyzing system comprising:

means for exciting a specimen for emission a plurality of times and making a spectroscopic analysis of the said specimen for each emission, means for detecting the light intensity of the spectral lines generated during each spectroscopic analysis;

means for storing light intensity data of the spectral lines;

means for specifying an emission in which the constituent element of said specimen and the non-constituent element of said specimen are contained over a predetermined level, said level being based on the light intensity data of the lines; and means for determining whether or not a composition of the constituent element and the non-constituent element is present at a portion of said specimen in accordance with said specified emission.

7. The spectroscopic analyzing system as set forth in claim 6, wherein said means for specifying comprises means for calculating the contents of each of said constituent elements based on the light intensity data and for specifying the level of said contents.

8. The spectroscopic analyzing method as set forth in claim 7, wherein said predetermined level is selected in accordance with an average value and a dispersion value of the contents for each emission.

9. The spectroscopic analyzing method as set forth in claim 6, wherein said means for exciting comprises means for spark discharging said specimen.

10. The spectroscopic analyzing method as set forth in claim 6, wherein said means for exciting comprises a laser beam.

11. The spectroscopic analyzing method as set forth in claim 10, and further comprising means responsive to said determination means for preparing a two-dimensional map of the composition determined; and display means for displaying the two-dimensional map.

* * * * *